(12) United States Patent
Singh et al.

(10) Patent No.: US 7,332,101 B2
(45) Date of Patent: Feb. 19, 2008

(54) PERMANENTLY LINKED, RIGID, MAGNETIC CHAINS

(75) Inventors: Harpreet Singh, Cambridge, MA (US); T. Alan Hatton, Sudbury, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 201 days.

(21) Appl. No.: 10/877,051

(22) Filed: Jun. 25, 2004

(65) Prior Publication Data
US 2005/0285073 A1    Dec. 29, 2005

(51) Int. Cl.
*H01F 7/00* (2006.01)

(52) U.S. Cl. .............................. 252/62.51 R; 428/372; 428/381; 428/384; 428/928; 252/62.51 C; 252/62.54; 252/62.55; 252/62.56; 252/62.57; 252/62.58; 252/62.59; 252/62.6; 252/62.61; 252/62.62; 252/62.63; 252/62.64

(58) Field of Classification Search ................ 501/32, 501/38, 12, 95.1, 95.2; 428/372, 928, 398; 252/62.51 R–62.64
See application file for complete search history.

(56) References Cited

U.S. PATENT DOCUMENTS

| | | | | |
|---|---|---|---|---|
| 4,797,378 A | * | 1/1989 | Sowman ................ | 501/95.1 |
| 5,096,551 A | * | 3/1992 | Schoen et al. ........... | 205/688 |
| 5,315,278 A | | 5/1994 | Demere et al. .......... | 335/282 |
| 5,831,376 A | | 11/1998 | Ho et al. ................ | 313/125 |
| 6,039,827 A | | 3/2000 | Cramer ................... | 156/173 |
| 6,180,005 B1 | | 1/2001 | Iannicelli ................ | 210/222 |
| 6,224,777 B1 | | 5/2001 | Iannicelli ................ | 210/695 |
| 6,527,972 B1 | * | 3/2003 | Fuchs et al. ............ | 252/62.54 |

OTHER PUBLICATIONS

Magnetorheological Fluids: Materials, Characterization, and Devices, Jour. Intel. Matl. Syst. Struct., vol. 7, Mar. 1996, pp. 123-130.*
Doyle, P.S., et al., "Self-Assembled Magnetic Matrices for DNA Separation Chips", Science, vol. 295, Mar. 22, 2002.
Biswal, S.L., et al., "Mechanics of Semiflexible Chains Formed by Poly(ethylene glycol)-Linked Paramagnetic Particles", Physical Review, Physical Review E 68. 021402-1-9 (2003).
Goubault, C., et al., "Flexible Magnetic Filaments As Micromechanical Sensors", The American Physical Society, vol. 91, No. 26, 260802-1-4.

* cited by examiner

*Primary Examiner*—C. Melissa Koslow
(74) *Attorney, Agent, or Firm*—Dana M. Gordon; Foley Hoag LLP (57) ABSTRACT

One aspect of the present invention relates to a permanently linked, rigid, magnetic chain of particles prepared by sol-gel methods. A second aspect of the present invention relates to a method of preparing a permanently linked, rigid, magnetic chain of particles comprising: coating a core material with one or more polyelectrolyte layers resulting in a coated particle; further coating the coated particle with a layer of magnetic nanoparticles resulting in a magnetic particle; coating the magnetic particle with a layer of a polycationic polyelectrolyte resulting in a coated magnetic particle; and applying a magnetic field to the coated magnetic particle in the presence of a metal oxide or metal oxide precursor capable of undergoing hydrolysis.

17 Claims, 9 Drawing Sheets

Magnetic Bead

12.5 μ spacer     25 μ spacer     90 μ spacer

PERMANENTLY LINKED, RIGID, MAGNETIC CHAINS

GOVERNMENT SUPPORT

The invention was made with support provided by the U.S. Army Research Office (DAAD-19-02-D0002); therefore, the government has certain rights in the invention.

BACKGROUND OF THE INVENTION

Magnetorheological (MR) fluids are suspensions of finely-divided paramagnetic particles that self-assemble to form chains under the application of an external magnetic field. This aggregation is reversible and, due to Brownian motion, the particles return to their freely dispersed state once the magnetic field is removed. Such chaining of MR fluids in the presence of an external magnetic field has a significant effect on the fluid rheology, including inducing a finite yield stress. Permanently linked chains of these polarizable particles have several interesting potential applications because their suspensions have a dynamic structure in the presence and absence of a magnetic field. S. L. Biswal, A. P. Gast, *Physical Review E* 2003, 68, 1402-1. They can be used as micromechanical sensors, for shock absorption in automobiles, headrests and ballistic events, and in DNA-separation and other bio-separation processes that use rigid obstacles (e.g., columns of aligned magnetic particles) to impede the convective transport of these species. C. Goubault, P. Jop, M. Fermigier, J. Baudry, E. Bertrand, J. Bibette, *Physical Review Letters* 2003, 9, 802-1; S. Deshmukh, G. H. McKinley, submitted to *Advanced Functional Material*; P. S. Doyle, J. Bibette, A. Bancaud , J. L. Viovy, *Science* 2002, 295, 2237. The rheological properties of these suspensions under different shear and magnetic field conditions may also have unique applications. To date, only flexible chains of superparamagnetic particles, linked permanently by a flexible polymer or other linker, have been reported. S. L. Biswal, A. P. Gast, *Physical Review E* 2003, 68, 1402-1; C. Goubault, P. Jop, M. Fermigier, J. Baudry, E. Bertrand, J. Bibette, *Physical Review Letters* 2003, 91, 802-1.

Remarkably, we have invented a technique whereby sol-gel chemistry is used to link permanently polarizable particles that have been aligned within a microchannel by an external magnetic field to yield rigid superparamagnetic chains.

SUMMARY OF THE INVENTION

The present invention relates to permanently linked, rigid, magnetic chains of particles prepared by sol-gel methods, compositions and devices comprising such chains, and methods of preparing such chains. Unlike previous magnetic chains, the magnetic chains of the present invention are both permanent and rigid. By permanent, it is meant that the chains maintain their linear structure even in the absence of a magnetic field. The combination of both properties is believed to impart unique mechanical and rheological properties to compositions comprising the magnetic chains.

In a further embodiment, the particles of the magnetic chains comprise a bead. In a further embodiment, the bead is a polymeric bead. In a further embodiment, the polymeric bead is coated with one or more layers of a polyelectrolyte. In a further embodiment, the bead is a polystyrene bead. In a further embodiment, the polystyrene bead is coated with one or more layers of a polyelectrolyte. In a further embodiment, the polystyrene bead is coated with three layers of a polyelectrolyte in the order: polycationic polyelectrolyte, polyanionic polyelectrolyte, polycationic polyelectrolyte. In a further embodiment, the polycationic polyelectrolyte is poly(diallyldimethyl) ammonium chloride and the polyanionic polyelectrolyte is polystyrene sulfonate. In a further embodiment, the particles further comprise a layer of magnetic nanoparticles. In a further embodiment, the magnetic nanoparticles comprise an iron oxide. In a further embodiment, the iron oxide is $Fe_2O_3$. In a further embodiment, the particles further comprise an outer layer of a polycationic polyelectrolyte. In a further embodiment, the particles are linked together permanently with a polymeric metal oxide. In a further embodiment, the metal oxide is $TiO_2$. In a further embodiment, the magnetic chain is hollow.

In another embodiment, the present invention relates to a composition or device comprising the permanently linked, rigid, magnetic chains of the present invention, wherein the device is a shock absorber, article of body armor, splint, micropump, valve, catalyst, therapeutic agent delivery system, or a mechanical stirrer. See, e.g., U.S. Pat. No. 6,720,710 ("Micropump").

In another embodiment, the present invention relates to a method of preparing a permanently linked, rigid, magnetic chain of particles comprising: a) coating a core material with one or more polyelectrolyte layers resulting in a coated particle; b) further coating the coated particle from step a) with a layer of magnetic nanoparticles resulting in a magnetic particle; c) coating the magnetic particle from step b) with a layer of a polycationic polyelectrolyte resulting in a coated magnetic particle; and d) applying a magnetic field to the coated magnetic particle from step c) in the presence of a metal oxide or metal oxide precursor capable of undergoing hydrolysis.

In a further embodiment the present invention relates to this method, wherein the core material is a bead. In a further embodiment, the core material is a polymeric bead. In a further embodiment, the core material is a polystyrene bead. In a further embodiment, the core material is coated with three layers of a polyelectrolyte. In a further embodiment, the core material is coated with three layers of a polyelectrolyte in the order: polycatioinic polyelectrolyte, polyanionic polyelectrolyte, polycationic polyelectrolyte. In a further embodiment, the polycationic polyelectrolyte is poly (diallyldimethyl) ammonium chloride and the polyanionic polyelectrolyte is polystyrene sulfonate. In a further embodiment, the magnetic nanoparticles comprise an iron oxide. In a further embodiment, the magnetic nanoparticles comprise $Fe_2O_3$. In a further embodiment, the magnetic field is applied across a microchannel comprising two glass microslides separated by a spacer with a magnet on each side of the microchannel. In a further embodiment, the magnetic field is applied for about 24 hours. In a further embodiment, the metal oxide is $TiO_2$ or the metal oxide precursor is a $TiO_2$ precursor. In a further embodiment, the $TiO_2$ precursor is titanium (IV) isopropoxide.

In a further embodiment, the method of preparing the magnetic chains of the present invention further comprises the step of removing the core material. In a further embodiment, the core material is removed by dissolving the core material in a solvent. In a further embodiment, the core material is removed by calcination. In a further embodiment, the calcination takes place at about 600° C.

These embodiments of the present invention, other embodiments, and their features and characteristics, will be apparent from the description, drawings and claims that follow.

DETAILED DESCRIPTION OF THE INVENTION

Overview

The rigid chains of the present invention are responsive to applied magnetic fields and have unique dynamic response characteristics and rheological properties. The particles used to form these chains are, for example, beads, in particular polymeric beads, such as polystyrene (PS) beads, that are coated with polyelectrolyte layers and magnetic nanoparticles, such as maghemite ($\gamma$-$Fe_2O_3$) nanoparticles. Once formed, the chains are linked together using sol-gel chemistry. For example, titanium dioxide precursors are hydrolyzed to create a rigid link between the beads giving a new class of magnetoresponsive materials. The extra strength imparted by the bonding material (titania in this case) ensures that the permanently linked rigid magnetic chains will be much stronger than those formed from free particles in suspension under a magnetic field, and hence will affect considerably the shock absorption and other mechanical properties of the magnetic fluid suspensions. In addition to bonding the linked chains permanently, the titania coating can be exploited in a range of other applications that include photocatalysis, sensor technology, and antimicrobial resistance. These rigid magnetic rods can also have potential microfluidic applications where they could be used, for example, as microstirrers, microvalves and micropumps. A. Terray, J. Oakey, D. W. M. Marr, *Science* 2002, 296, 1841; and U.S. Pat. No. 6,720,710.

Definitions

For convenience, before further description of the present invention, certain terms employed in the specification, examples and appended claims are collected here. These definitions should be read in light of the remainder of the disclosure and understood as by a person of skill in the art.

Unless defined otherwise, all technical and scientific terms used herein have the same meaning as commonly understood by a person of ordinary skill in the art.

The articles "a" and "an" are used herein to refer to one or to more than one (i.e., to at least one) of the grammatical object of the article. By way of example, "an element" means one element or more than one element.

The term "anatase" is art-recognized and refers to a transparent to nearly opaque tetragonal mineral form of $TiO_2$.

The term "colloidal" is art-recognized and relates to a substance comprised of small particles suspended in a continuous medium, such as a liquid, a solid, or a gaseous substance.

The terms "comprise" and "comprising" are used in the inclusive, open sense, meaning that additional elements may be included.

The term "copolymer" is used to mean a polymer of two or more different monomers.

The term "covalent bond" is art-recognized and refers to a bond between two atoms where electrons are attracted electrostatically to both nuclei of the two atoms, and the net effect of increased electron density between the nuclei counterbalances the internuclear repulsion. The term covalent bond includes coordinate bonds when the bond is with a metal ion.

The term "including" is used to mean "including but not limited to". "Including" and "including but not limited to" are used interchangeably.

The phrase "permanently linked" as used herein refers to a magnetic chain of particles wherein the particles maintain their chain structure even in the absence of a magnetic field.

The term "polyelectrolyte" is art-recognized and refers to a polymer producing large chain-type ions in solution. A polyelectrolyte may be natural, such as protein, or synthetic. Poly(diallyldimethyl) ammonium chloride is an example of a polycationic polyelectrolyte and polystyrene sulfonate is an example of a polyanionic polyelectrolyte.

The term "polymer" is used to mean a large molecule formed by the union of repeating units (monomers). The term polymer also encompasses copolymers.

The term "rheology" is art-recognized and refers to the science of the flow and deformation of matter, generally organic and inorganic liquids with suspended particles.

The phrase "sol-gel methods" is art-recognized and refers to the formation of interconnections in a network of colloidal particles.

The term "therapeutic agent" is art-recognized and refers to any chemical moiety that is a biologically, physiologically, or pharmacologically active substance that acts locally or systemically in a subject. Examples of therapeutic agents, also referred to as "drugs", are described in well-known literature references such as the Merck Index, the Physicians Desk Reference, and The Pharmacological Basis of Therapeutics, and they include, without limitation, medicaments; vitamins; mineral supplements; substances used for the treatment, prevention, diagnosis, cure or mitigation of a disease or illness; substances which affect the structure or function of the body; or pro-drugs, which become biologically active or more active after they have been placed in a physiological environment. Antibiotic agents and Fab I/Fab K inhibitors are examples of therapeutic agents.

The term "therapeutic effect" is art-recognized and refers to a local or systemic effect in animals, particularly mammals, and more particularly humans caused by a pharmacologically active substance. The term thus means any substance intended for use in the diagnosis, cure, mitigation, treatment or prevention of disease or in the enhancement of desirable physical or mental development and/or conditions in an animal or human. The phrase "therapeutically-effective amount" means that amount of such a substance that produces some desired local or systemic effect at a reasonable benefit/risk ratio applicable to any treatment. The therapeutically effective amount of such substance will vary depending upon the subject and disease condition being treated, the weight and age of the subject, the severity of the disease condition, the manner of administration and the like, which can readily be determined by one of ordinary skill in the art. For example, certain compositions of the present invention may be administered in a sufficient amount to produce a at a reasonable benefit/risk ratio applicable to such treatment.

For purposes of this invention, the chemical elements are identified in accordance with the Periodic Table of the Elements, CAS version, *Handbook of Chemistry and Physics*, $67^{th}$ Ed., 1986-87, inside cover.

Core Material

The core material that undergoes surface modification by polyelectrolytes, subsequent magnetization, and sol-gel coordination to form the permanently linked, rigid, magnetic chains of the present invention can be any material suitable in size and shape to form a colloidal suspension. The core material may be permanent, in which case it remains within the chains of the present invention, or it may be non-permanent, in which case after acting as a template for chain formation the core material is removed, leaving behind hollow magnetic tubes. When the core material is non-permanent, the core material may be removed either chemically by dissolving the core material in a suitable solvent, or by calcination.

When the core material is a polymer or copolymer, a wide range of polymers or copolymers may be used. In certain embodiments, the polymers or co-polymers of the subject magnetic chains have molecular weights ranging from about 2000 to about 1,000,000 daltons. Preferably, the molecular weights are at least about 10,000, 20,000, 30,000, 40,000, or 50,000 daltons, more preferably at least about 100,000 daltons, and even more preferably at least about 250,000 daltons. Number-average molecular weight (Mn) may vary widely, but generally will fall in the range of about 1,000 to about 200,000 daltons, or the range from about 1,000 to about 100,000 daltons, or the range from about 1,000 to about 50,000 daltons.

Non-limiting examples of polymeric cores include poly-l-lysine (PL) or poly-D-lysine; poly-alpha, beta-(2-aminoethyl)-D,L-aspartamide; poly-l-aspartic acid; poly-glutamic acid, copolymers of histidine with positively or negatively charged amino acids, polyethyleneimines, i.e., polyethylene imines; natural saccharides or products chemically derived thereof, which may be exemplified by: galacturonic acid, glucuronic acid, mannuronic acid, hyaluronic acid, pectic acid, neuraminic acid, alginic acid, carrageenan; oxidized dextrans; aminated, e.g. containing linked aminogroups, polysaccharides or oligosaccharides, linear or branched. Such oligosaccharides may be obtained by chemical alteration of, e.g., dextran, mannan, xylan, pullulan, cellulose, chytosan, agarose, fucoidan, galactan, arabinan, fructan, fucan, chitin, pustulan, levan or pectin. In addition these poly- or oligosachharides may be represented by heteropolymers or homopolymers of monosaccharides such as glucose, galactose, mannose, galactose, deoxyglucose, ribose, deoxyribose, arabinose, fucose, xylose, xylulose, ribulose, polyamidoamine, linear or branched; polyacrylic acid; polystyrene, polyalcohols, e.g., polyvinylalcohol an polyxylitol.

Other polymers include poly(phosphoesters), poly(lactides), poly(glycolides), poly(caprolactones), poly(anhydrides), poly(amides), poly(urethanes), poly(esteramides), poly(esters), poly(dioxanones), poly(acetals), poly(ketals), poly (carbonates), poly(orthocarbonates), poly(phosphazenes), poly(hydroxybutyrates), poly(hydroxy-valerates), poly (alkylene oxalates), poly(alkylene succinates), poly(malic acids), poly(amino acids), poly(vinylpyrrolidone), poly(ethylene glycol), poly(hydroxycellulose), chitin, chitosan, and copolymers, terpolymers, or combinations or mixtures of the above materials. For additional examples of polymers suitable for use in the present invention, see U.S. Pat. Nos. 6,509,323; 6,492,560; 6,468,532; 6,521,736; 6,348,069; 5,871,710; and 6,051,549. In a preferred embodiment, the polymeric core is polystyrene in the shape of a bead.

Polyelectrolytes

Surface modification of the core material is carried out in a layer-by-layer process using polyelectrolytes to alter the surface charge. For example, if the core material is sulfonated polystyrene, the inherently negative surface can be made positive by applying a layer of a cationic polyelectrolyte. Similarly, a positively charged core material may be layered with an anionic polyelectrolyte to create a negative outer surface. More than one layer of polyelectrolyte may be added in a stepwise fashion to the core material. For example, upon a negatively-charged core material, a cationic/anionic/cationic trilayer may be applied to yield a particle with a positively-charged outer surface.

Examples of polyectrolytes include polymers capable of producing large chain-type ions in solution, i.e., a macromolecular substance, which, on dissolving in water or another ionizing solvent, dissociates to give polyions (polycations or polyanions)—multiply charged ions—together with counterions for charge balance. Polyelectrolytes dissociating into polycations and polyanions, with no ions of small charge, are also contemplated. A polyelectrolyte can be a polyacid, a polybase, a polysalt or a polyampholyte. The polyelectrolyte may comprise a hydrophilic homopolymer or a hydrophilic copolymer wherein the monomer comprising the homopolymer, and at least one monomer comprising the copolymer, is ionizable. Although the polyelectrolyte may contain water-insoluble segments, the polyelectrolytes are water-soluble, i.e., they will form aqueous dispersions or solutions. Alternatively, the aqueous phase may comprise a monomer having an ionized or ionizable functional group, which when polymerized, produces the polyelectrolyte.

For a water-soluble polyelectrolyte or for ionic or ionizable monomers, the ionic or ionizable groups may be cationic, anionic or both. For polyelectrolytes that contain water-insoluble segments, the ionic groups can be cationic or anionic, but typically should all have the same type of charge. The like charges cause the copolymer domains to repel each other, thereby inhibiting particle flocculation. Reduction of particle flocculation is desired because flocculation decreases layer uniformity on the core particle.

The polymer chain of the polyelectrolyte may be linear or branched. The polyelectrolyte(s) comprise at least one ionizable monomeric component, such as an acid group, and are electrolytic in an aqueous medium. Examples of suitable monomeric materials that can provide electrolytic and ionizable moieties include, but are not limited to, for example, 2-acrylamido-2-methyl-1-propanesulfonic acid (AMPS), salts of sulfopropyl acrylate, maleic anhydride, itaconic anhydride, β-carboxy ethylacrylate, vinylazlactone-glycolic acid adduct, sodium styrene sulfonate, potassium acrylate, sodium acrylate, sodium methacrylate, ammonium acrylate, sodium 2-acrylamido-2-methylpropane sulfonate, 4,4,9-trimethyl-4-azonia-7-oxa-dec-9-ene-1-sulfonate, N,N-dialkyl-N-beta-methacryloxyethyl ammonium propionate betaine, trialkylamine (meth)acrylamide, 1,1-dimethyl-1-(2,3-dihydroxypropyl)amine methacrylamide, and other zwitterionic ethylenically-unsaturated monomers having the requisite solubility requirements, mixtures thereof, and the like. Preferred polar monomers include those selected from the group consisting of acrylamide, sodium styrene sulfonate, sodium acrylate, sodium 2-acrylamido-2-methylpropane sulfonate, sodium methacrylate, and mixtures thereof, due to ease of formulation and desirable properties when polymerized, or combinations of these materials.

Useful co-monomers that may be used to prepare the copolymeric polyelectrolytes include any ethylenically unsaturated monomers that may be co-polymerized with the ionizable monomer. Examples of useful co-monomers include olefins, such as ethylene and propylene; vinyl monomers; vinylidene monomers; monoolefinic and polyolefinic monomers; and heterocyclic monomers. In another embodiment, co-monomers include substituted or unsubstituted ethylenically unsaturated carboxylic acids or derivatives thereof. The carboxylic acids can be mono- or poly-carboxylic acid derivatives. Useful carboxylic acid derivatives include esters, amides, nitriles, and anhydrides. In another embodiment, the co-monomers include, for example, alkyl acrylates having 1-4 carbon atoms (e.g., butyl acrylate).

It is also possible to use a polymerizable mixture to prepare the polyelectrolyte in situ, in which case the aqueous phase further comprises a water-soluble photoinitiator. Water-soluble photoinitiators useful in the present invention are photoinitiators which generate free radicals on exposure to actinic (usually ultraviolet) radiation which act as initiators for the copolymerization of the ionomers, and, when present, the co-monomers.

Non-limiting examples of polyelectrolytes that may be used to alter the surface charge of the core material include polyacrylic acid, polymethacrylic acid, polyethylenesulphonic acid, polyvinylsulphonic acid, polystyrenesulphonic acid, polyvinylphenylsulphuric acid (phenol ester) maleic acid/alkene copolymer, maleic acid/vinyl alkyl ether copolymer, polyglutamic acid, polysilicic acid, polyphosphoric acid, polysaccharides, chitosan, polylysine, and the corresponding copolymers with neutral amino acids, polyvinylamine, polyethyleneimine, polyviny-4-alkylpyridinium salt, polysilicic salt, polyshosphoric salt, polysaccharide salts, poly(methylene)-N,N-dimethylpiperidinium salt, poly (vinylbenzyltrimethylammonium) salt, dextran, heparin, polyallylamines, sulfonated polystyrene, polyallylamine hydrochloride, sulfonated polyaniline, poly(diallyldimethyl) ammonium chlorides and tetrahydrothiophenium precursor polyelectrolyte of polyvinylpyrole. This list is not intended to be an exhaustive listing of all the polyelectrolytes that can be affixed to the surface of the core material. Natural polyelectrolytes can also be affixed to the core material surface (e.g. DNA, proteins, and silk). Polyelectrolytes affixed to the substrate surface may also have a variety of molecular arrangements (e.g. linear, hyperbranched, or star-like). Mixtures of like charged polyelectrolytes may also be used to form an individual layer on the core material.

Magnetic Nanoparticles

The magnetic nanoparticles that coat the surface modified beads and allow chain formation in an applied magnetic field can be any nanoparticles composed of ferromagnetic or ferrimagnetic material having domains that are aligned in such a way as to produce a net magnetic field outside the substance. Non-limiting examples of magnetic nanoparticles include nanoparticles of magnetic metal oxides which may include Fe either as Fe(II), Fe(III), or a mixture of Fe(II)/Fe(III). Non-limiting examples of such oxides include FeO, $Fe_2O_3$ (maghemite), and $Fe_3O_4$ (magnetite). The magnetic nanoparticles may also be a mixed oxide of the type $M1_xM2_{3-x}O_4$, wherein M1 represents a divalent metal ion and M2 represents a trivalent metal ion. For example, the magnetic nanoparticles may be magnetic ferrites of the formula $M1Fe_2O_4$, wherein M1 represents a divalent ion selected from the following: Mn, Co, Ni, Cu, Zn, or Ba, pure or in admixture with each other or in admixture with ferrous ions. Other metal oxides include aluminium oxide, chromium oxide, copper oxide, manganese oxide, lead oxide, tin oxide, titanium oxide, zinc oxide and zirconium oxide or metals, such as Fe, Cr, Ni or magnetic alloys. If the nanoparticles contain $Fe_3O_4$ or $Fe_2O_3$ or Fe or Cr or Ni or magnetic alloys, then the nanoparticles are magnetic.

Suitable materials referred to as being soft magnetic are metals based on the pure elements Fe, Ni, Cr and alloys thereof preferably based on Ni. Non-limiting examples of such alloys are known under the name permalloy. They are composed of 70 to 80% Ni with additives of Cr, Cu and Mo. Other magnetic nanoparticles not listed here, but known to one of ordinary skill in the art, may be used to align the surface modified beads in the presence of an external magnetic field to form the permanently linked, rigid chains of the present invention.

Sol-gel Permanent Linkage

Sol-gel chemistry produces a variety of inorganic networks from silicon or metal alkoxide monomer precursors. Through this process, homogeneous inorganic oxide materials with desirable properties of hardness, optical transparency, chemical durability, tailored porosity, and thermal resistance, can be produced at room temperatures, as opposed to the much higher melting temperatures required in the production of conventional inorganic glasses. The uses of sol-gel-produced glasses and ceramics are typically based on the various material shapes generated in the gel state, i.e., monoliths, films, fibers, and mono-sized powders.

The sol-gel process, as the name implies, involves the evolution of inorganic networks through the formation of a colloidal suspension (sol) and gelation of the sol to form a network in a continuous liquid phase (gel). The precursors for synthesizing these colloids consist of a metal or metalloid element surrounded by various reactive ligands. Metal alkoxides are most popular because they react readily with water. Metal alkoxides, such as aluminates, titanates, and borates, are commonly used in the sol-gel process. At the functional group level, three reactions are generally used to describe the sol-gel process: hydrolysis, alcohol condensation, and water condensation. However, the characteristics and properties of a particular sol-gel inorganic network are related to a number of factors that affect the rate of hydrolysis and condensation reactions, such as, pH, temperature and time of reaction, reagent concentrations, catalyst nature and concentration, aging temperature and time, and drying.

After adsorption of the magnetic nanoparticles on the surface modified core material, the material is suspended in a solvent with a metal or metal coating precursor. In one embodiment the metal precursor is a titania precursor, such as titanium (IV) isopropoxide (TIP). Hydrolysis of TIP creates polymeric $TiO_2$ which creates the permanent and rigid bond between the coated core material to give permanent chains even after removal of the magnetic field. Other metal coatings and metal-coating precursors known to one of ordinary skill in the art may be used in sol-gel methods to create the permanent link. Non-limiting examples of metal precursors that may be used to form the permanent link include precursors of $FeTiO_3$, $H_2Ti_4O_9$, $CaTiO_3$, $MgTiO_3$, $MnTiO_3$, $CoTiO_3$, $NiTiO_3$, $SrTiO_3$, $BaTiO_3$, $Mg_2TiO_4$, $PbTiO_3$, $Zn_2TiO_4$, $Co_2TiO_4$, $BaTiO_3$, $Ba_2TiO_4$, $Ba_4Ti_{13}O_{30}$, $B_6Ti_{17}O_{40}$, $TiZrO_2$, $ZrSiO_4$, $HfO_2$, $VO_2$, $V_2O_5$, $NbO_2$, $Nb_2O_5$, $TaO_2$, $Ta_2O_5$, $Cr_2O_3$, $CrO_2$, $CrO_3$, $MoO_2$, $MoO_3$, $PbMoO_4$, $MgMoO_4$, $WO_2$, $WO_3$, $FeWO_4$, $MnWO_4$, $CaWO_4$, $PbWO_4$, $MnO_2$, $Mn_3O_4$, $ReO_2$, $ReO_3$, $Re_2O_3$, $Re_2O_5$, $Re_2O_7$, $TcO_2$, $TcO_3$, $Tc_2O_7$, $CoO$, $CoO_2$, $Co_2O_3$, $Co_3O_4$, $NiO$, $PtO$, $PdO$, $CuO$, $Cu_2O$, $AgO$, $ZnO$, $CdO$, $MgO$, $CaO$, $SrO$, $BaO$, $B_2O_3$, $Al_2O_3$, lanthanum modified $PbTiO_3$, $Ba(Mg_{1/3}Ta_{2/3})O_3$, $TiO_2$ containing Au and Ag metal particles, $BaSr_{1-x}TiO_3$, $Pb(Mg,Zn)_{1/3}Nb_{2/3}O_3$, lead iron niobate, lead barium niobate, lead magnesium niobate, $SiO_2$, Ba-ferrite, $Bi_4Ti_3O_{12}$, ZnO, silica-$TiO_2$, and $Pb_{1-x}La_xTi_{1-x/4}O_3$.

Synthesis and Properties of Permanently Linked, Rigid, Magnetic Chains

Figure 1:
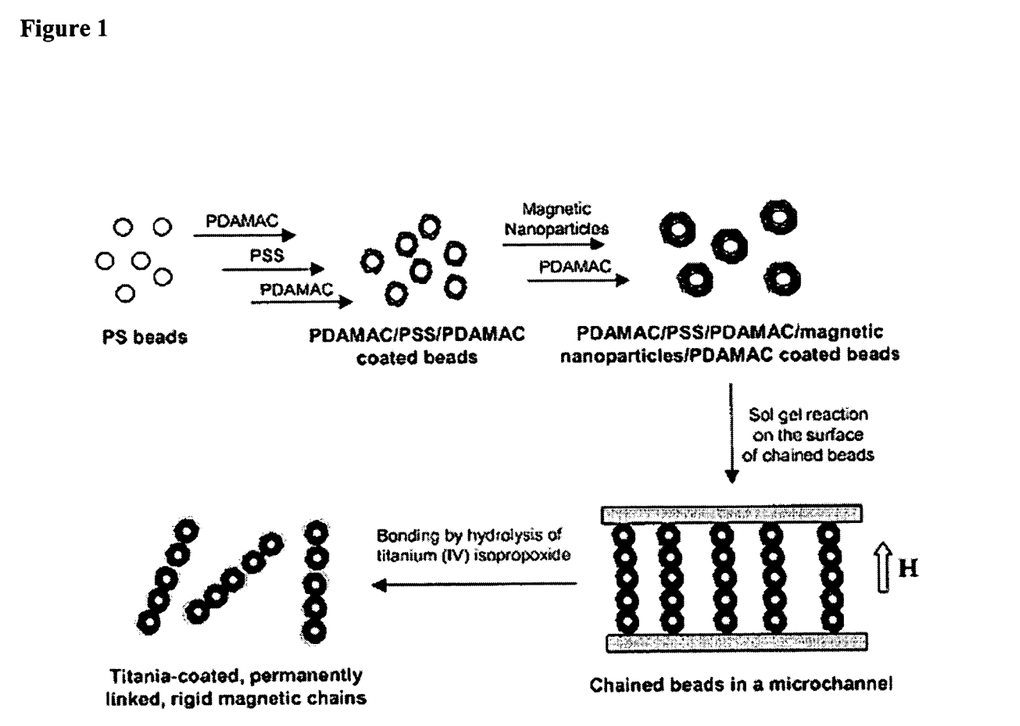
FIG. 1 depicts a process for producing permanently linked rigid magnetic chains.

FIG. 1 outlines a procedure for making the rigid magnetic chains. Positively charged superparamagnetic PS beads were prepared using a layer-by-layer (LbL) strategy as described by Caruso et al. F. Caruso, R. A. Caruso, H. Mohwald, *Science* 1998, 282, 111; F. Caruso, A. S. Susha, M. Giersig, H. Mohwald, *Advanced Materials* 1999, 11, 950. First, poly (diallydimethyl) ammonium chloride (PDAMAC) was adsorbed onto negatively charged sulfonated polystyrene (PS) beads (790 nm). This step was followed by the adsorption of a negatively charged polyelectrolyte, polystyrene sulfonate (PSS) and, finally, of a second layer of PDAMAC to leave the coated particles positively charged. The reversal of surface charge was monitored by measuring the zeta potential (Zeta Pals, Brookhaven) after each coating. The measured zeta potential was 50 mV when PDAMAC was the outer layer and –60 mV when the outer layer was PSS. The positively charged beads (PS coated with PDAMAC/PSS/PDAMAC) were then coated with negatively charged citrate-stabilized magnetic nanoparticles (Zeta potential=–20 mV) followed by a layer of PDAMAC so that the final surface charge was positive. These positively charged beads were recovered and resuspended in anhydrous ethanol. The outer PDAMAC layer on the PS beads was highly hygroscopic and retained some of its water of hydration even when suspended in anhydrous ethanol. From a Karl Fischer titration, the partition coefficient for water between the bead surface and the bulk ethanol was measured to be ~60.

Figure 2:
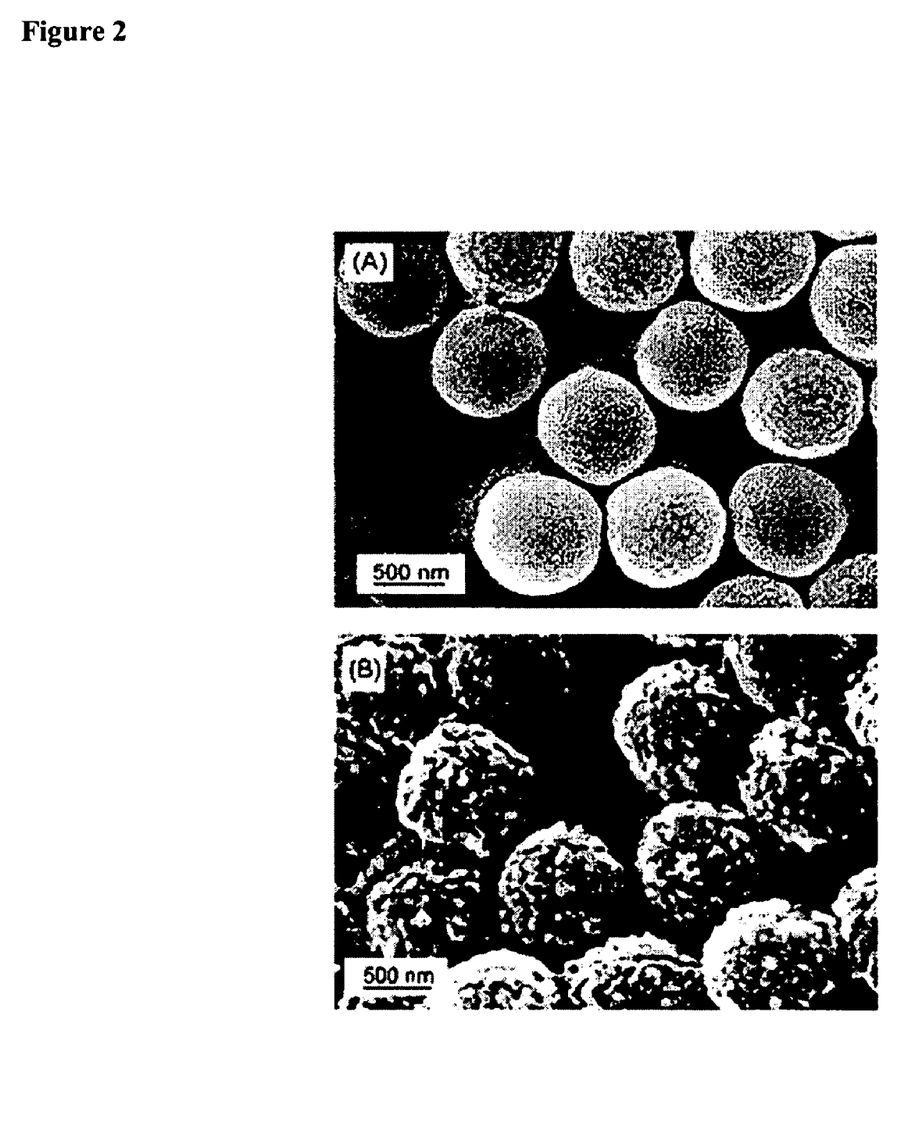
FIG. 2 depicts SEM micrographs of (A) plain PS beads and (B) magnetic nanoparticle-coated beads. The samples were sputter-coated with gold for better contrast. The thickness of the magnetic coating was estimated to be 25 nm based on the difference in the diameters of the coated and the uncoated beads.
Figure 3:
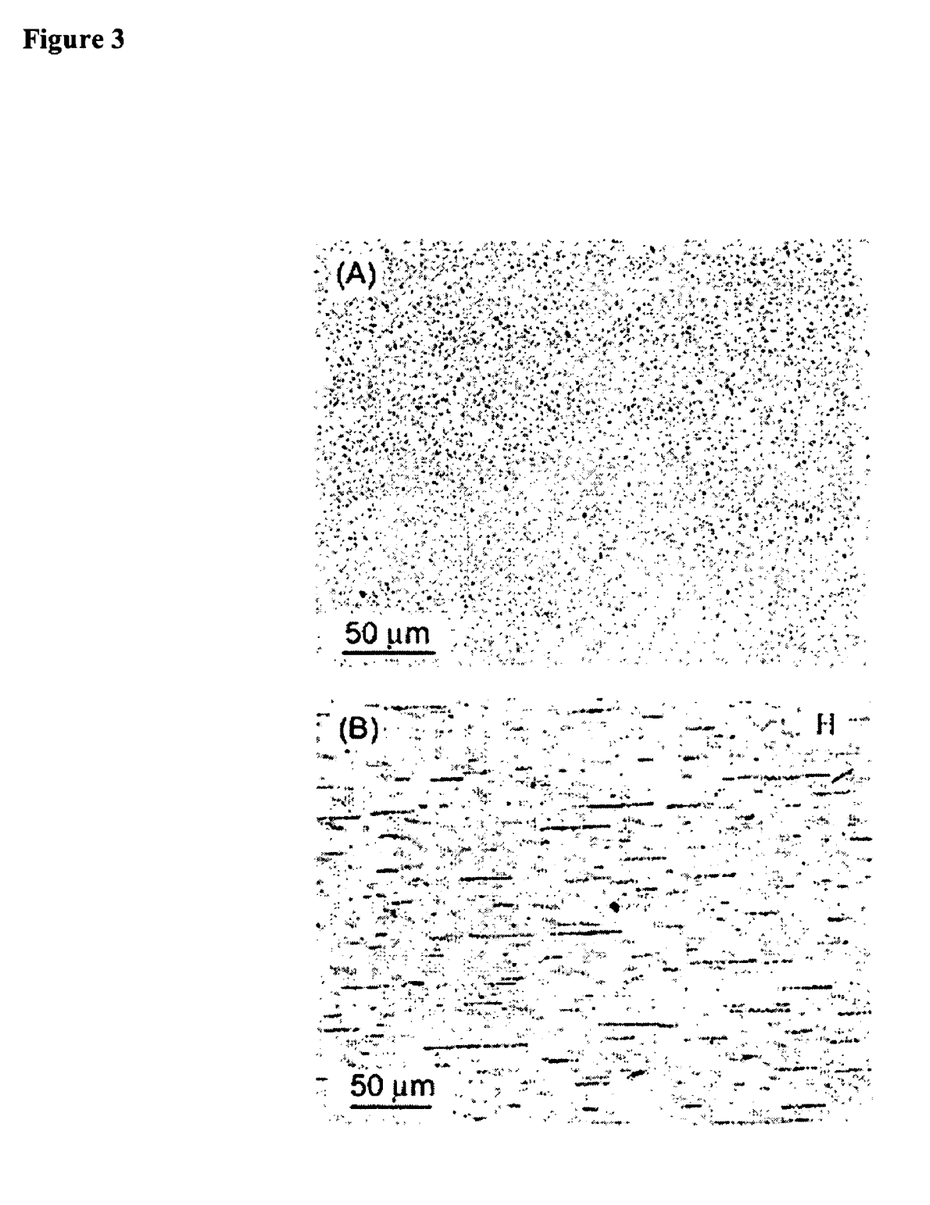
FIG. 3 depicts magnetic beads in (A) the absence, and (B) the presence of an external applied magnetic field as observed under an optical microscope.

The adsorption of the magnetic nanoparticles on the positively charged PS beads produced completely covered beads, as observed by scanning electron microscopy (JEOL-6060SEM). See FIG. 2. The thickness of the magnetic nanoparticle coating was 25 nm, in close agreement with our estimate of 27 nm based on the quantity of PS beads and magnetic nanoparticles added to the suspension. Magnetization experiments on these coated beads indicated that they had zero remanence, thus verifying the superparamagnetic nature of the particles. The beads, which were well dispersed as individual particles in the absence of an applied magnetic field, aggregated reversibly as chains under an applied magnetic field. See FIGS. 3A and 3B, respectively.

The coated bead suspension in ethanol was mixed with a titania precursor (titanium (IV) isopropoxide, TIP) and injected into a microchannel (25 μm×50 mm×25 mm). The beads aligned into chains upon application of a magnetic field across the channel, the height of which determined the length of the chains formed. The hydrolysis reaction was allowed to proceed in the presence of the magnetic field for 24 h. The controlled nucleation of titania on the surfaces of the aligned beads cemented the particles within the chains together and produced permanently linked rigid superparamagnetic chains. The localized concentration of water on the outer PDAMAC ensured preferential hydrolysis of TIP on the bead surface. A small degree of hydrolysis was observed in the bulk due to the low concentration of water in the solvent, but this did not have an effect on the properties of the chains formed during this process.

Figure 4:
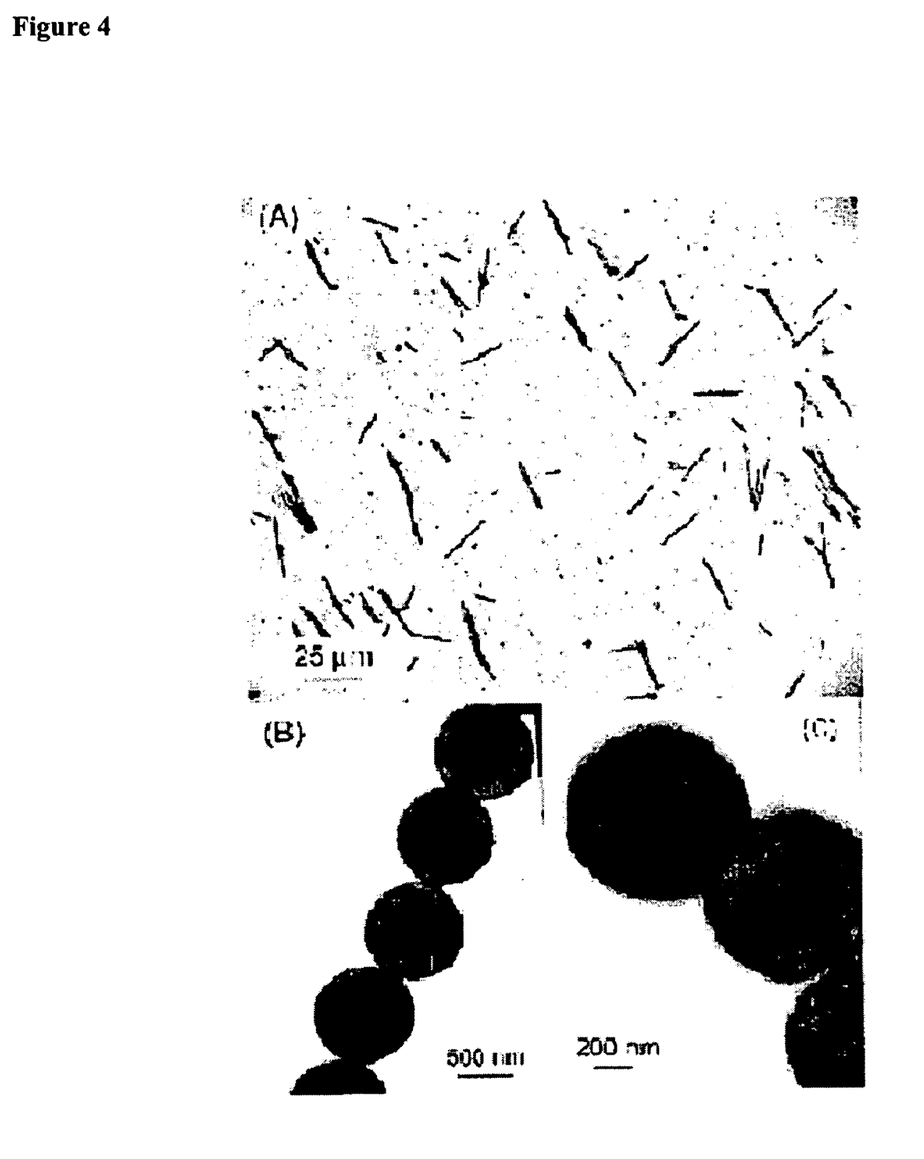
FIG. 4 depicts TEM micrographs of titania-coated magnetic chains. The thickness of the titania coating was estimated to be 30 nm.

The positive charge on the PS beads also contributed to the efficient capture of the nucleated titania. Titania is negatively charged at neutral pH, and the positive charge on the magnetic beads from the outermost PDAMAC layer ensured that the nucleated titania associated with the particle surface. E. A. Barringer, H. K. Bowen, *Langrnuir* 1985, 1, 420. The charge on the bead surface reversed from positive to negative as the adsorption of titania continued. During this process of charge reversal, some of the beads became negatively charged, while others were positively charged. The aggregation of oppositely charged beads, which inhibited the formation of chains, was prevented by adding poly-(vinylpyrrolidone) (PVP) to the suspension, which adsorbed on both titania particles and the magnetic bead surfaces to impart a steric stabilization against bead aggregation. J. N. Smith, J. Meadows, P. A. Williams, *Langmuir* 1996, 12, 3773. At the end of the reaction, permanently linked rigid magnetic chains were formed. These chains were stable and could be recovered and stored for months without degradation. Transmission electron microscopy (JEOL 2000X, 200 kV) indicated a titania coating thickness of 30 nm, that was close to the thickness (32 nm) calculated based on the concentrations of TIP and PS beads used in the experiments. See FIG. 4. The titania-coated magnetic rods aligned in the direction of an externally applied magnetic field.

Figure 5:
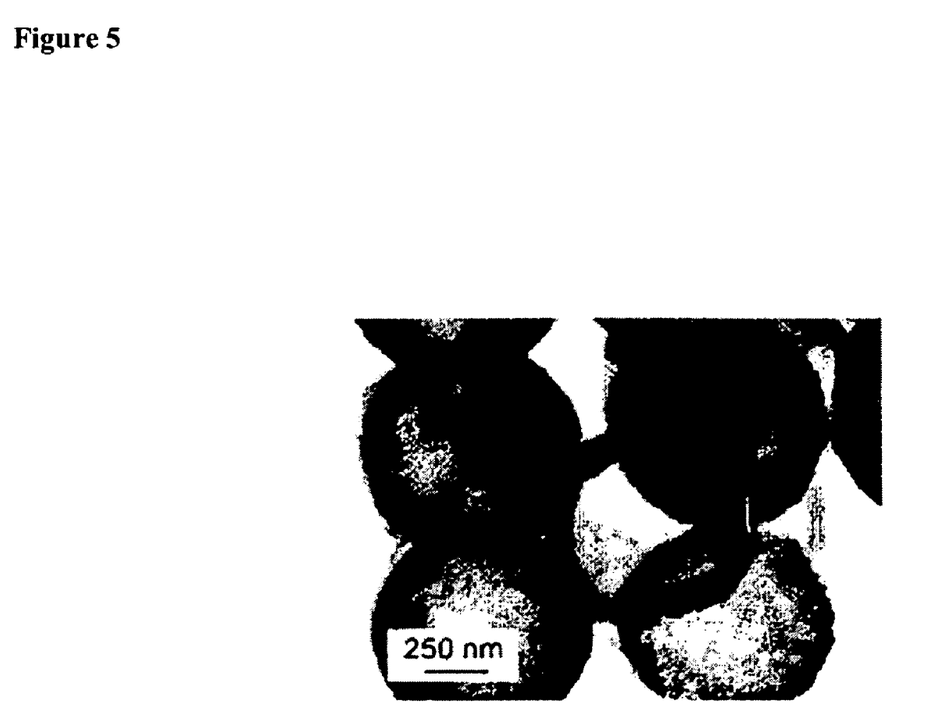
FIG. 5 depicts TEM micrographs of hollow titania-linked magnetic chains after calcination. The transparency of the beads in the micrograph provides evidence of their hollow structure.

The permanently linked magnetic chains were calcined at about 600° C. to convert the amorphous titania to its crystalline anatase form, as confirmed by X-ray diffraction. The anatase form of titania has a higher mechanical strength and a much wider range of application possibilities than does the amorphous form of this oxide. I. A. Balcioglu, I. Arslan, *Environmental Pollution* 1998, 103, 261. During the calcination process, the PS beads burned off to yield magnetic chains that consisted of hollow spherical cores linked together by the titania coating. See FIG. 5.

The approach used here for making rigid magnetic chains is versatile, as it should allow the synthesis of magnetoresponsive rods using a variety of sol-gel precursors and a variety of magnetic nanoparticles. The intrinsic and extrinsic properties of the chain can also be readily manipulated. The diameter and length of the chains can be controlled by changing the PS bead diameter and the height of the microchannel, respectively. The magnetization of the beads can be enhanced by depositing additional magnetite layers on the particle surfaces, following the established layer-by-layer technique. Potential areas of interest and application lie in the dynamic response of these rigid magnetic chains to applied magnetic fields, and on methods for the production of these chains on a continuous basis.

Macrostructures

Although chains are exemplified in the present disclosure, one of ordinary skill in the art can readily envision macrostructures in other dimensions. For example, due to the magnetic dipoles of the beads coated with the magnetic nanoparticles, when beads of different sizes were used, smaller beads were able to position themselves adjacent to the chains of the larger beads, overcoming the repulsion normally seen between the chains of equal sized beads. One can readily see how adjusting parameters such as bead size, chains may form adjacent to each other such that upon hydrolysis of the metal precursor a permanently linked, rigid plane would form. Similarly, several planes permanently linked to each would form a platform. Thus, other macrostructures besides chains are considered part of the present invention.

Applications

The permanently linked, rigid magnetic chains of the present invention have promising applications in the medical sciences and biotechnology. Such applications include, but are not limited to, magnetically enhanced cell-separation, protein-separation, or DNA-separation and in vivo therapeutic agent targeting. In vivo therapeutic agent targeting may be carried out by selective adsorption of medicines within the hollow chains of the present invention which can be enriched subsequently in specific tissue of the body by applying external magnetic fields. The slow diffusion of the therapeutic agent out of the hollow magnetic chains results in a new type of sustained release system. This type of directing the magnetic fluids to particular sites within tissue has also been discussed for such promising uses as retina repair treatment.

Biological applications of magnetic colloids and particles have been reported in such diverse areas as applying very small forces or torques to DNA molecules, directly measuring colloidal force-distance profiles, targeting and isolating biomolecules or cells, and, more recently, separating large DNA fragments. Smith, S. B., Finzi, L., Bustamante, C., *Science,* 1992, 258, 1122; Strick, T. R., Allemand, J. F., Bensimon, D., Bensimon, A., Croquette, V., *Science,* 1996, 271, 1835; Calderon, F. L., Stora, T., Monval, O. M., Poulin, P., Bibette, J., *Phys. Rev. Lett.,* 1994, 72, 2959; Newman, D., Price, C., *Principles and Practice of Immunoassay* (MacMillan Reference, London, 1997), Chapter 8; Doyle, P. S., Bibette, J., Bancaud, A., Viovy, J. L., *Science,* 2002, 295, 2237.

Equally interesting are the many mechanical applications that make use of magnetic nanoparticles and the magnetic fluids that comprise them. The remarkable properties of the magnetic fluids (long-term stability, high magnetic saturation and initial magnetic susceptibility, low viscosity and vapor pressure, absence of a significant aggregation, stability in gravitation fields, and fair thermal conductivity) render them suitable for many applications, including but not limited to:

1. intensification of heat transfer;
2. high speed rotary seals with zero linkage and low maintenance, e.g. for hard disk drives ('liquid O-ring);
3. damping element for voice coil in loudspeaker systems;
4. heat carriers;
5. magnetic inks for inkjet printing, e.g., for bar coding and signatures read by magnetic recording technology;
6. magnetic separation on non magnetic materials (recycling technology);
7. shock absorbers; and
8. measuring devices, transducers, sensors, etc.

For instance, magnetic fluids offer various opportunities to build several classes of sensors for mechanical, electromagnetic and aerodynamic and hydrodynamic measurements. Rosenzweig, R. E., *Ferrohydrodynamics,* Cambridge Univ. Press 1985; I. Anton, I. De Sabata, L. Vekas, *Application oriented researches on magnetic fluids,* Jour. Mag. Mag. Mater. 85, 219, 1990; K. Raj, B. Moskowitz, R. Casciari, *Advances in ferrofluid technology,* Jour. Mag. Mag. Mater. 149, 174, 1995. In particular, the use of magnetic fluids in accelerometer design and construction is favored, due to fulfillment of the necessary accelerometer elements: mass suspension, elastic constant, inertial mass, proportional damping, magnetofluidic levitation servoloop. M. I. Piso, *Magnetic Liquid Accelerometers,* Rom. Jour. Phys. 47, 437, 1995. Several types of accelerometers and inclinometers were achieved, their field of application extending from oilrig survey to basic research. Sensitivities in the range from $10^{-10}$ to 100 $ms^{-2}$, frequency domains from static to several $10^3$ Hz and precision up to 16 bit were obtained. K. Raj, B. Moskowitz, R. Casciari, *Advances in ferrofluid technology,* Jour. Mag. Mag. Mater. 149, 174, 1995; M. I. Piso, *Magnetic Liquid Accelerometers,* Rom. Jour. Phys. 47, 437, 1995.

For advanced applications, the permanently linked, rigid magnetic chains of the present invention may be used for terrestrial tides and seismic monitoring, geophysical surveys, inertial guidance, those sensors are competitive in performance with the superconducting devices. Both linear and angular movement could be sensed by magnetic fluid aided sensors or even by some intrinsic effects of the magnetofluidic material.

Additionally, the permanently linked, rigid magnetic chains of the present invention may also be used as chemical sensors and catalysts. For example, when the chains are hollowed out either chemically or by calcination, the resulting hollow tubes have a high degree of surface area ideal for sensors and catalysts. The metal coating that creates the permanent properties of the chains, provides an ideal surface for metal catalysis. It is envisioned that heterogeneous catalytic reactions associated with metal surfaces, for example photocatalysis, may be carried out on the chains of the present invention. It is also envisioned that sensors for agents, such as nerve gas, which are known to comprise similar compounds and surfaces as those of the magnetic chains will be able to utilize the magnetic chains of the present invention with greater sensitivity.

Improved response shock absorbers utilizing magnetic fluids is another area garnering a lot of attention. This type of magnetic fluid shock absorber responds instantaneously to a modulated current feed of only a few amps from a conventional 12-volt system. The shock absorber fluid is generally about 40% magnetic material, but with the current off, the oil flows freely. When the current is applied (generally up to five amps per shock), an electromagnetic coil is energized in the shock absorber piston, thickening the fluid as it flows through the piston orifices. This "stiffens" the shock, and the amount of stiffness is infinitely variable depending on the amount of current applied. The response time of the shock is $\frac{1}{1000}$ of a second, less than a tenth of the time required by the premium-priced electronically-controlled valves in the shock absorbers of contemporary automobiles. To date, only magnetic particles of low order have been used. It is envisioned that ordered chains will have an even greater effect upon the thickening of the oil through the piston orifices.

MR fluids have also found use as micropumps and valves for liquids. The basic idea of a MR fluid micropump is to generate magnetically a pressure to pump the liquid. Greivell, N., Hannaford, B., *IEEE Trans. Biomed. Eng.,* 1997, 44, 129; Hatch, A. et al., *J. Microelectromech. Syst.,* 2001, 10, 215; Bohm, S., Olthuis, W., Bergveld, P., *Sens. Actuators A, Phys.,* 1999, 77, 223; Khoo, M., Liu, C., *Proc. 22$^{nd}$ EMBS,*

Chicago, Jul. 23-28, 2000, 3, 2394; Santra, S., Holloway, P., Batich, C. D., *Sens. Actuators B, Chem.*, 2002, 87, 358. Pressure is created by displacing an MR fluid plug that plays the role of a piston in a channel, or pressure may be created by actuating an integrated magnetic membrane comprising the MR fluid. Yamahata, C., Gijs, M. A. M., *IEEE*, 2004, 458. Actuation of an MR fluid plug may also be used to open and close a pathway creating valve with less moving parts.

Recent work has also incorporated MR fluids into body armor. The goal is to incorporate the switchable MR fluid into the material currently used to make bullet-proof vests, which is essentially a woven fabric full of air gaps. Once the fabric is immersed in an MR fluid what is obtained without a magnetic field is a very soft, very flexible fabric, and when a magnetic field is applied the stiffness of the fabric changes by a factor of about fifty. Eventually, the fabric-fluid combination could resist a shockwave or shrapnel. Since troops won't be carrying magnets on the battlefield, fabric of military uniforms would be wired with electric current that soldiers could switch on to produce electromagnetic fields. The idea behind this "instant armor" may also be applied to other forms of fabrics, such as splints, which are also encompassed by the current invention.

The permanent and rigid magnetic chains of the present invention may also be used as a mechanical stirrer. Switching an external magnetic field on and off causes an almost instantaneous alignment and relaxation, respectively, of the magnetic chains within a fluid system. This type of motion results in mixing on a colloidal-particle scale.

Magnetic nanoparticles have also found use in magnetic ink toners for reprographic applications. Reprographic processing involves the formation of printed images on sheet substrates, such as paper. Examples of reprographic processing include the printing of facsimile transmissions, making of photocopies, and printing of electronically-stored information from a computer. Technological developments over the last several years have made available high quality, relatively low-cost facsimile machines, photocopiers and printers for black print applications. The same low cost, high quality options are not available, however, for color print applications.

One proposal for reducing the dulling and distortion of color caused by magnetic particles is to use nanoparticle $\gamma$-$Fe_2O_3$ as the magnetic particles. R. F. Ziolo et al., Matrix-Mediated Synthesis of Nanocrystalline gamma-$Fe_2O_3$: A New Optically Transparent Magnetic Material, Science, vol 257, July 1992, pp. 219-223. Due to their small size, such particles would likely be more transparent than the larger magnetic particles currently used in toner compositions and, therefore, would not distort colors to the same extent.

EXEMPLIFICATION

The invention now being generally described, it will be more readily understood by reference to the following examples which are included merely for purposes of illustration of certain aspects and embodiments of the present invention, and are not intended to limit the invention.

Example 1

Synthesis of Positively Charged PS Beads

Commercially available negatively charged sulfonated PS beads (average diameter 790 nm, Spherotech) were made positively charged using a layer-by-layer polyelectrolyte adsorption technique. In a typical process, 0.5 mL of a 0.5 wt % solution of PS beads was suspended in an aqueous solution of 0.5 mL of 1 mg/mL PDAMAC (poly (diallydimethyl) ammonium chloride, MW 150,000, Aldrich, 0.5 M NaCl). After 30 min of adsorption, the beads were separated by centrifugation at 7000 g for 10 min and resuspended in water. This process was repeated three times. The beads were then coated with a negatively charged polyelectrolyte by suspending them in a 1 mg/mL of polystyrene sulfonate (PSS, MW 70,000, Aldrich, 0.5 M NaCl) solution using the same process outlined above. These negatively charged PS beads were finally coated with a second layer of PDAMAC by the above method to obtain positively charged particles.

Example 2

Synthesis of Magnetic Nanoparticles and Subsequent Adsorption

Citrate-coated magnetic nanoparticles with an average diameter of 10 nm (as estimated by TEM) were synthesized using Massart's method. R. Massart, 1981, Pat. 19810205 CAN 94:113532. An aqueous solution of magnetic nanoparticles (150 µL, concentration 0.005 wt % in water) was added to the positively charged PDAMAC/PSS/PDAMAC coated PS beads (1 mL, concentration 0.25 wt % in water). After continuous shaking for 30 min, maghemite-coated PS beads were recovered by centrifugation at 7000 g for 10 min. They were again coated with PDAMAC using the same procedure to yield positively charged magnetic beads. These beads were then centrifuged and washed with anhydrous ethanol four times, and resuspended in anhydrous ethanol.

Example 3

Linking of Magnetic Beads

Figure 6:
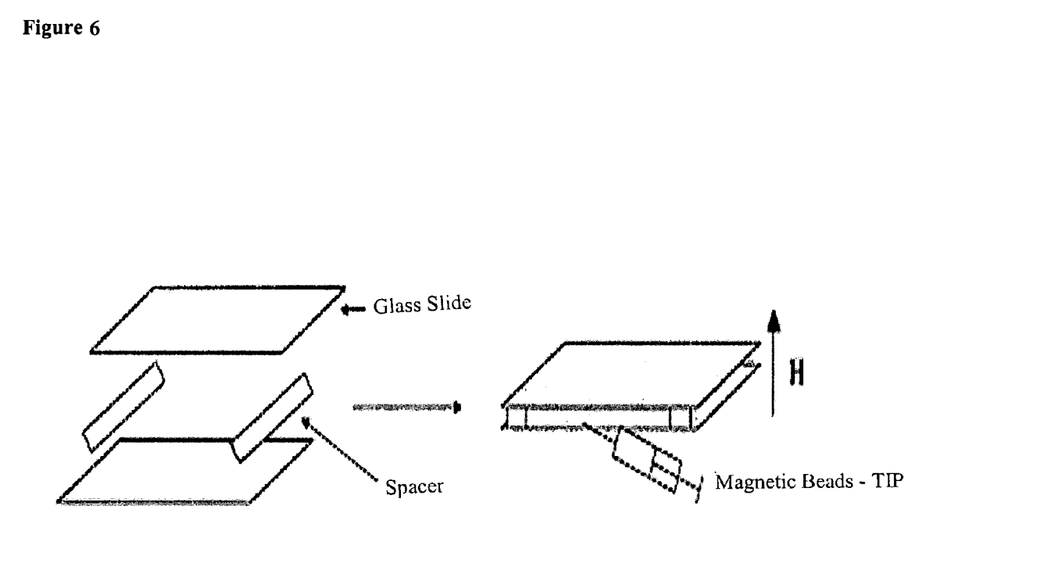
FIG. 6 depicts the microchannel reaction system used to prepare the permanently linked, magnetic chains of the present invention.
Figure 7:
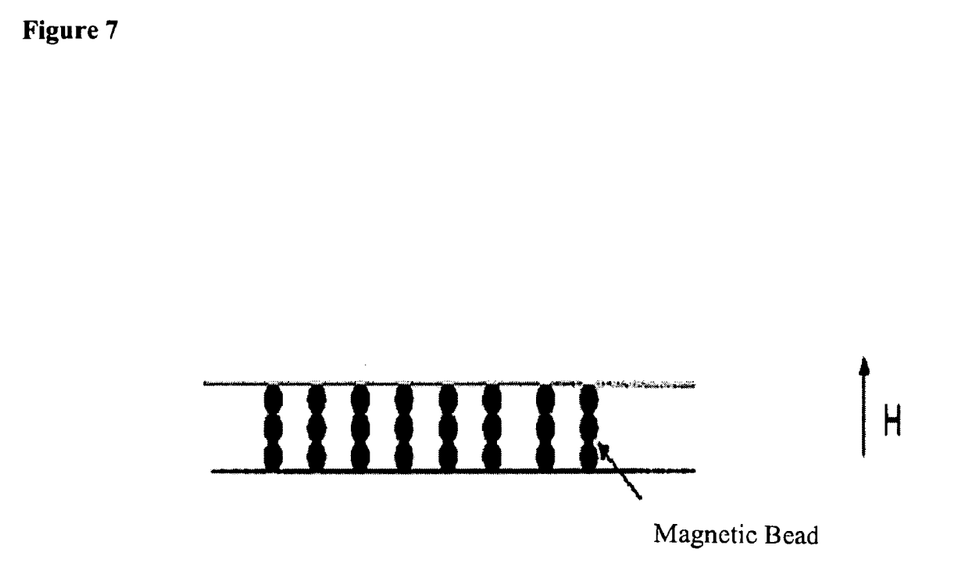
FIG. 7 depicts the chaining of beads in the direction of the magnetic field (H).
Figure 8:
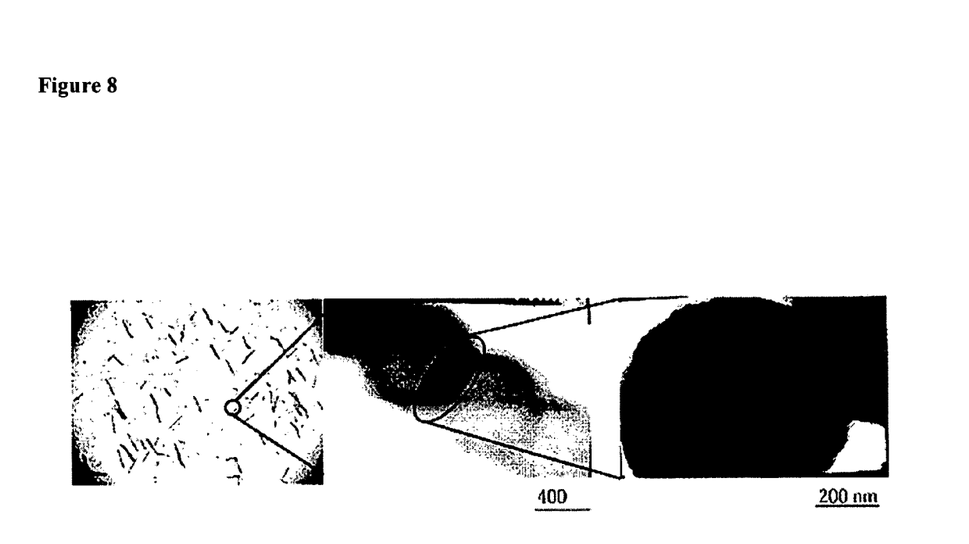
FIG. 8 depicts the permanently linked, magnetic chains of the present invention.

A microchannel was prepared using two glass microslides (25 mm×75 mm) that were separated by a teflon spacer (90 pm thick, FIG. 6). In a typical reaction a mixture of 0.5 mL (10 mg/mL) of PDAMAC coated magnetic PS beads, 5 mg of Poly (vinylpyrrolidione) (PVP, MW 1,300,000) and 3 µL of titanium isopropoxide (TIP, 99 wt %) was injected in the microchannel. PVP was added to avoid aggregation of the beads. An orthogonal magnetic field was applied with two rectangular neodymium-iron-boron magnets (0.2 T). The magnetic beads aggregated to form chains in the direction of the magnetic field. FIG. 7. The length of the chain was limited by the spacer thickness. The localized presence of water on the surface of the beads lead to the hydrolysis of TIP on the bead surface to yield titania which bonded the beads together resulting in permanently linked magnetic chains. FIG. 8. The reaction was carried out for 24 hours under applied magnetic field in an ethanol-saturated chamber to prevent evaporation from the microchannel reaction mixture. At the end of the reaction the chains were recovered easily and could be stored for a long period of time without any sign of degradation. The technique developed is very versatile and it is possible to produce magnetic chains linked with different materials, including zirconia, silica, tin oxide, tungsten oxide etc. The hollow magnetic beads can also be chained and bonded using the same technique. The length and diameter of the chains can be controlled by changing the spacer thickness and the diameter of the PS beads respectively.

Figure 9:
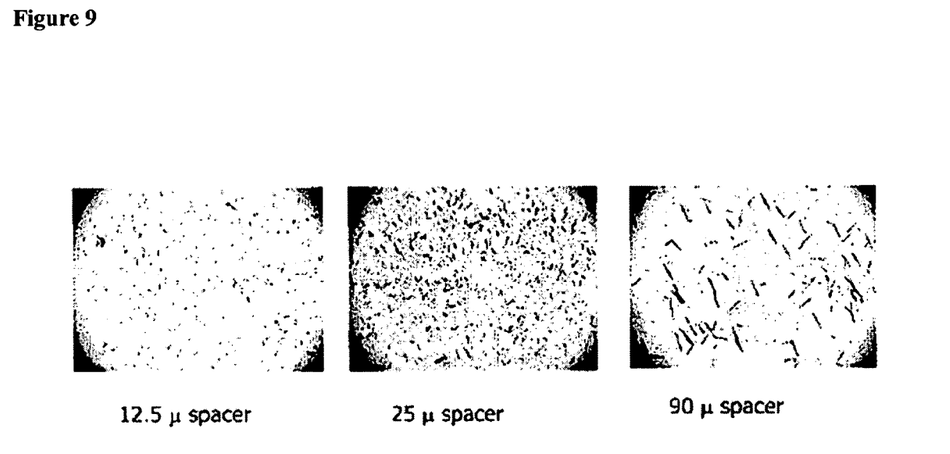
FIG. 9 depicts the effect of spacer thickness on the chain length. Average chain length is 7.6 μm, 13 μm, and 19 μm, respectively.

Magnetic chains of different length ranging from 10 pm to 20 µm were synthesized with different spacer thickness. FIG. 9. These chains are magnetic in nature and align in the direction of magnetic field.

Example 4

Sample Preparation

TEM samples were prepared by drying a drop of sample on a carbon substrate grid. SEM studies were performed by drying the sample on a carbon tape grid. The zeta potentials of the samples were measured in water (MilliQ, conductivity 18 MΩ). Karl Fisher titrations (Mettler Toledo DI-31) of the positively charged magnetic beads were conducted by centrifugation of a suspension in anhydrous ethanol, analysis of the supernatant and the centrifuged beads, and a partition coefficient calculated based on the water content difference between the two samples. For calcinations, samples were first dried in a refractive crucible in a furnace, heated to 600° C. at a rate of 5° C./min, held at 600° C. for 8 h, and then cooled to room temperature at a rate of 5° C./min.

INCORPORATION BY REFERENCE

All of the publications, U.S. patents, and U.S. published patent applications cited herein are hereby incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

We claim:

1. A permanently linked, rigid, magnetic chain, comprising a plurality of colloidal-sized particles, wherein:
    (a) each of said particles comprises a first layer, wherein said first layer comprises a magnetic metal oxide;
    (b) each of said particles optionally comprises a core material; and
    (c) said particles are linked together with a second layer, wherein said second layer comprises a homogeneous inorganic oxide.
2. The magnetic chain of claim 1, wherein said core material is present and is a bead.
3. The magnetic chain of claim 1, wherein said core material is present and is a polymeric bead.
4. The magnetic chain of claim 1, wherein said core material is present and is a polystyrene bead.
5. The magnetic chain of claim 1, wherein said core material is present and is a polymeric bead coated with one or more layers of a polyelectrolyte.
6. The magnetic chain of claim 1, wherein said core material is present and is a polystyrene bead coated with one or more layers of a polyelectrolyte.
7. The magnetic chain of claim 1, wherein each of said particles comprises a polystyrene bead coated with three layers of a polyelectrolyte in the order: polycationic polyelectrolyte, polyanionic polyelectrolyte, polycationic polyelectrolyte.
8. The magnetic chain of claim 7, wherein the polycationic polyelectrolyte is poly(diallyldimethyl) ammonium chloride and the polyanionic polyelectrolyte is polystyrene sulfonate.
9. The magnetic chain of claim 1, wherein the magnetic metal oxide comprises an iron oxide.
10. The magnetic chain of claim 7, wherein the magnetic metal oxide is an iron oxide.
11. The magnetic chain of claim 9, wherein the iron oxide is $Fe_2O_3$.
12. The magnetic chain of claim 10, wherein the iron oxide is $Fe_2O_3$.
13. The magnetic chain of claim 1, wherein the particles further comprise an outer layer of a polycationic polyelectrolyte.
14. The magnetic chain of claim 10, wherein the particles further comprise an outer layer of a polycationic polyelectrolyte.
15. The magnetic chain of any one of claims 1-8 or 9-14, wherein the homogenous inorganic oxide is $TiO_2$.
16. The magnetic chain of claim 1, wherein said core material is absent.
17. A composition comprising the magnetic chain of any one of claims 1-8, 9-14, 15, or 16.

* * * * *